(12) United States Patent
Kolchin et al.

(10) Patent No.: US 10,215,713 B2
(45) Date of Patent: *Feb. 26, 2019

(54) DETERMINING A CONFIGURATION FOR AN OPTICAL ELEMENT POSITIONED IN A COLLECTION APERTURE DURING WAFER INSPECTION

(71) Applicant: KLA-Tencor Corporation, Milpitas, CA (US)

(72) Inventors: Pavel Kolchin, Fremont, CA (US); Mikhail Haurylau, San Jose, CA (US); Junwei Wei, Milpitas, CA (US); Dan Kapp, Pleasanton, CA (US); Robert Danen, Pleasanton, CA (US); Grace Chen, Los Gatos, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/626,123

(22) Filed: Jun. 18, 2017

(65) Prior Publication Data

US 2017/0292918 A1 Oct. 12, 2017

Related U.S. Application Data

(63) Continuation of application No. 14/749,564, filed on Jun. 24, 2015, now Pat. No. 9,709,510.
(Continued)

(51) Int. Cl.
*G01N 21/00* (2006.01)
*G01N 21/95* (2006.01)
(Continued)

(52) U.S. Cl.
CPC ......... *G01N 21/9501* (2013.01); *G01N 21/47* (2013.01); *G01N 21/8806* (2013.01);
(Continued)

(58) Field of Classification Search
CPC ......... G01N 21/9501; G01N 21/95623; G01N 2201/0668; G01N 2021/8887;
(Continued)

(56) References Cited

U.S. PATENT DOCUMENTS

2006/0186361 A1 8/2006 Weiss et al.
2006/0262297 A1* 11/2006 Matsui ............... G01N 21/8806
356/237.5
(Continued)

FOREIGN PATENT DOCUMENTS

CN 1532542 9/2004
CN 102636963 8/2012
(Continued)

*Primary Examiner* — Isiaka Akanbi
(74) *Attorney, Agent, or Firm* — Ann Marie Mewherter

(57) ABSTRACT

Methods and systems for determining a configuration for an optical element positioned in a collection aperture during wafer inspection are provided. One system includes a detector configured to detect light from a wafer that passes through an optical element, which includes a set of collection apertures, when the optical element has different configurations thereby generating different images for the different configurations. The system also includes a computer subsystem configured for constructing additional image(s) from two or more of the different images, and the two or more different images used to generate any one of the additional image(s) do not include only different images generated for single collection apertures in the set. The computer subsystem is further configured for selecting one of the different or additional configurations for the optical element based on the different images and the additional image(s).

40 Claims, 5 Drawing Sheets

Related U.S. Application Data

(60) Provisional application No. 62/017,264, filed on Jun. 26, 2014, provisional application No. 62/111,402, filed on Feb. 3, 2015.

(51) Int. Cl.
  *G01N 21/956* (2006.01)
  *G01N 21/47* (2006.01)
  *G01N 21/88* (2006.01)

(52) U.S. Cl.
  CPC ....... *G01N 21/8851* (2013.01); *G01N 21/956* (2013.01); *G01N 21/95623* (2013.01); *G01N 2021/8887* (2013.01); *G01N 2201/0668* (2013.01)

(58) Field of Classification Search
  CPC .. G01N 21/956; G01N 21/8806; G01N 21/21; G01B 9/04; G02B 21/006; G01J 3/0229; G01J 3/18; G01J 3/2803
  USPC .............................. 356/237.1–237.6; 382/149
  See application file for complete search history.

(56) References Cited

U.S. PATENT DOCUMENTS

| | | |
|---|---|---|
| 2012/0206703 A1 | 8/2012 | Bhattacharyya et al. |
| 2013/0059240 A1* | 3/2013 | Van Der Schaar ......................... G03F 7/70633 430/30 |
| 2013/0148114 A1* | 6/2013 | Berlatzky ............ G01N 21/956 356/237.5 |
| 2013/0258310 A1* | 10/2013 | Smilde ................ G03F 7/70633 355/77 |
| 2014/0139830 A1* | 5/2014 | Lange ................. G01N 21/9501 356/237.5 |
| 2014/0146322 A1 | 5/2014 | Hill et al. |
| 2014/0252200 A1 | 9/2014 | Garsha et al. |
| 2014/0354983 A1* | 12/2014 | Kolchin ............ G01N 21/9501 356/237.5 |
| 2016/0033877 A1 | 2/2016 | Smilde et al. |

FOREIGN PATENT DOCUMENTS

| | | |
|---|---|---|
| CN | 103201682 | 7/2013 |
| JP | 2014-530389 | 11/2014 |

* cited by examiner

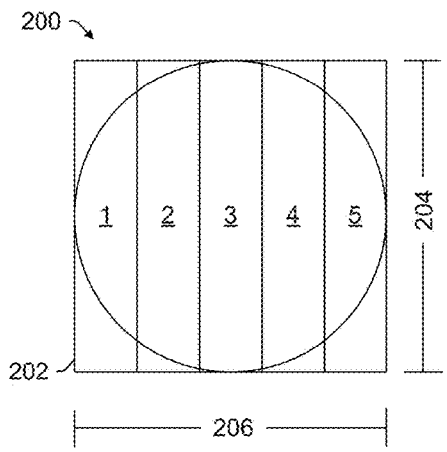
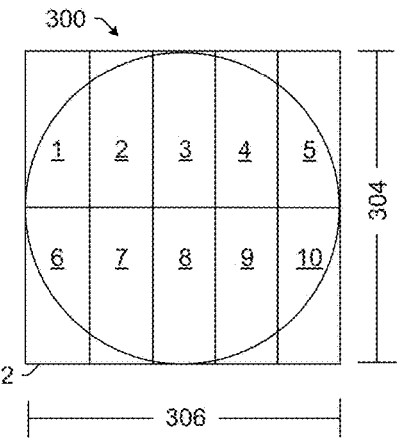
Fig. 2                     Fig. 3
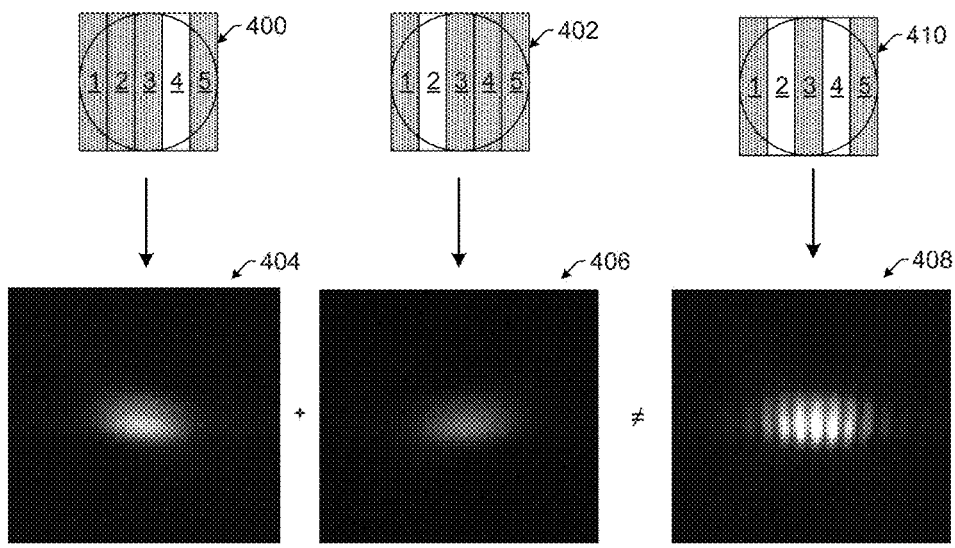
Fig. 4

DETERMINING A CONFIGURATION FOR AN OPTICAL ELEMENT POSITIONED IN A COLLECTION APERTURE DURING WAFER INSPECTION

BACKGROUND OF THE INVENTION

1. Field of the Invention

This invention generally relates to methods and systems for determining a configuration for an optical element positioned in a collection aperture during wafer inspection. This invention may also include determining a configuration for a complimentary optical element positioned in an illumination aperture during wafer inspection.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Many inspection tools have adjustable parameters for many of the optical elements of the tools. In this manner, the parameters for one or more optical elements (such as light source(s), polarizer(s), lens(es), detector(s), and the like) can be altered depending on the type of wafer being inspected and the characteristics of the defects of interest (DOIs) on the wafer. For example, different types of wafers may have dramatically different characteristics, which can cause the same tool with the same parameters to image the wafers in extremely different ways. In addition, since different types of DOIs can have dramatically different characteristics, inspection system parameters that are suitable for detection of one type of DOI may not be suitable for detection of another type of DOI. Furthermore, different types of wafers can have different noise sources, which can interfere with detection of DOIs on the wafers in different ways.

The number of adjustable parameters of wafer inspection tools, while advantageous in that the wafer inspection tools can be used for inspection of many different types of wafers and DOIs, means that a substantial number of different combinations of parameter values (otherwise referred to as "modes") need to be (or should be) considered when setting up a wafer inspection recipe. For example, in order to ensure that the best possible mode available on an inspection system is selected for use in an inspection recipe, a significant number of the modes should be considered. Otherwise, the probability that the best possible mode has been evaluated and then subsequently chosen may be relatively low.

Setting up inspection process recipes that are suitable for wafer inspection is, therefore, a non-trivial process that must often be repeated for each different type of wafer that will be inspected. As such, many different methods and systems for setting up wafer inspection recipes have been developed to make recipe setup easier and more efficient. However, not all wafer inspection recipe setup methods and systems can be used for all types of light and/or all types of inspection systems. For example, systems and methods that are created for setup of wafer inspection recipes that use coherent light may not necessarily be suitable for setup of wafer inspection recipes that use incoherent light. In addition, wafer inspection recipe setup for optimizing illumination with one type of light (e.g., incoherent light) may not necessarily be suitable for optimizing collection/detection with the same type of light.

Accordingly, it would be advantageous to develop methods and systems for determining a configuration for an optical element positioned in a collection aperture during wafer inspection that do not have one or more of the disadvantages described above.

SUMMARY OF THE INVENTION

The following description of various embodiments is not to be construed in any way as limiting the subject matter of the appended claims.

One embodiment relates to a system configured to determine a configuration for an optical element positioned in a collection aperture during wafer inspection. The system includes a light source configured to generate light that is directed to the wafer. The system also includes an optical element positioned in a collection pupil plane. The optical element includes a set of collection apertures. In addition, the system includes a detector configured to detect light from the wafer that passes through the optical element when the optical element has different configurations thereby generating different images for the different configurations. At least one of the different configurations includes only a single collection aperture in the set, and at least another of the different apertures includes two of the collection apertures in the set.

The system further includes a computer subsystem configured for constructing one or more additional images from two or more of the different images. The two or more different images used to generate any one of the one or more additional images do not include only the different images generated for single collection apertures in the set. The computer subsystem is further configured for determining one or more characteristics of the different images and the one or more additional images, comparing the one or more characteristics of the different images and the one or more additional images, and selecting one of the different or additional configurations for the optical element for inspection of the wafer based on results of the comparing step. The system may be further configured as described herein.

Another embodiment relates to a non-transitory computer-readable medium storing program instructions executable on a computer system for performing a computer-implemented method for determining a configuration for an optical element positioned in a collection aperture during wafer inspection. The computer-implemented method includes acquiring different images for a wafer. The different images were generated by directing light generated by a light source to the wafer and detecting light from the wafer that passes through an optical element when the optical element has different configurations thereby generating the different images for the different configurations. The optical element and the different configurations are configured as described above. The computer-implemented method also includes the constructing, determining, comparing, and selecting performed by the computer subsystem of the system described above. The computer-readable medium may be further configured as described herein. The steps of the computer-implemented method may be performed as described further herein. In addition, the computer-implemented method for which the program instructions are executable may include any other step(s) of any other method(s) described herein.

Another embodiment relates to a method for determining a configuration for an optical element positioned in a collection aperture during wafer inspection. The method includes the directing and detecting steps that are performed as described above to generate the different images. The method also includes the constructing, determining, comparing, and selecting performed by the computer subsystem of the system described above, which are performed by a computer system in the method.

Each of the steps of the method described above may be performed as described further herein. The method described above may include any other step(s) of any other method(s) described herein. The method described above may be performed using any of the systems described herein.

BRIEF DESCRIPTION OF THE DRAWINGS

Other objects and advantages of the invention will become apparent upon reading the following detailed description and upon reference to the accompanying drawings in which:

FIGS. 2-3 are schematic diagrams illustrating plan views of embodiments of an optical element that includes a set of collection apertures;

FIG. 4 is a schematic diagram illustrating plan views of embodiments of different configurations of the optical element shown in FIG. 2 and examples of different images that may be generated using the different configurations;

Figure 1:
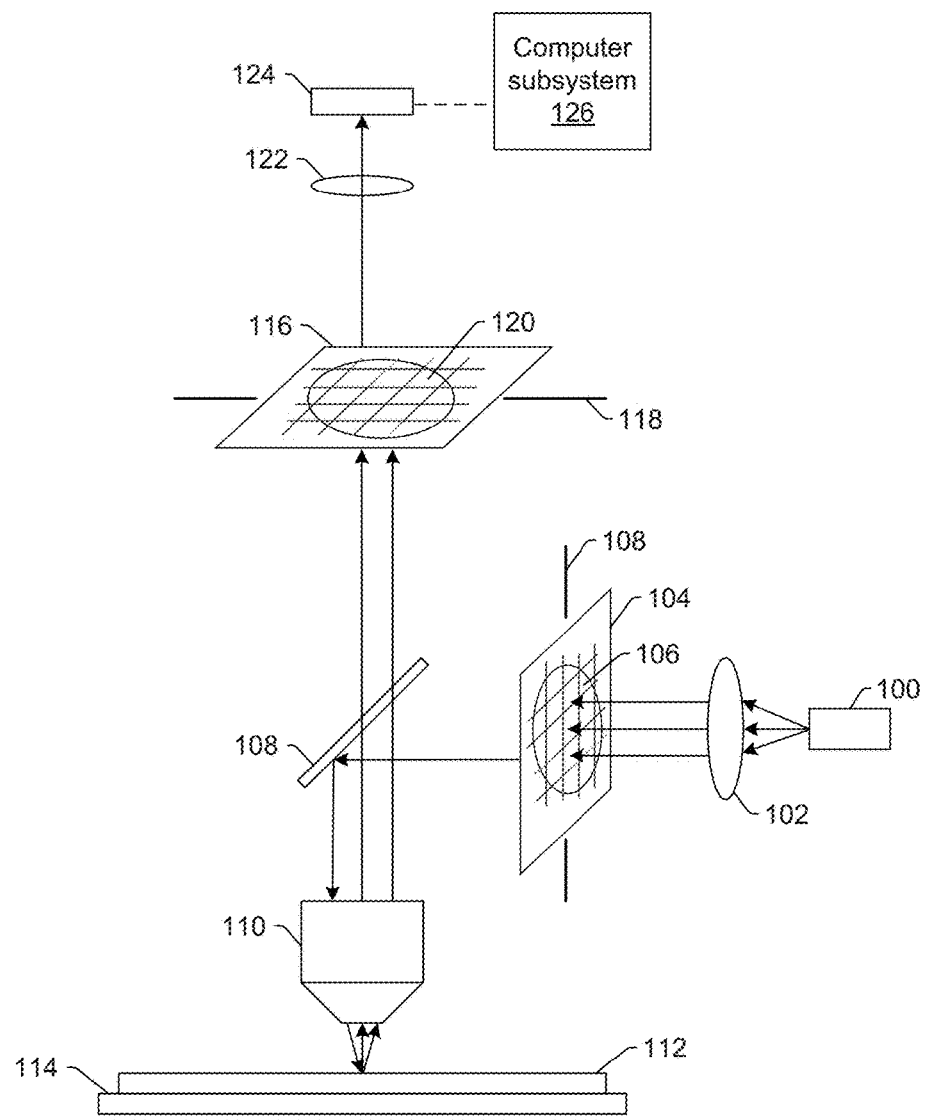
FIG. 1 is a schematic diagram illustrating a side view of one embodiment of a system configured as described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to determine a configuration for an optical element positioned in a collection aperture during wafer inspection. As will be described further herein, the embodiments can be used for image reconstruction to optimize the collection aperture and mode to thereby enhance defect detection. For example, as described further herein, the embodiments provide systems and methods for enhancing and optimizing defect detection by finding the optimal configuration of a collection blocking or phase contrast aperture, which is placed in the collection pupil plane of an inspection system. The configuration (e.g., shape) of the aperture that results in higher sensitivity may be the output of the embodiments described herein, which may include image reconstruction that may be performed as described further herein. The embodiments can also be used to increase the detection rate of defects of interest (DOIs) and/or simultaneously reduce the detection rate of nuisance events. In addition, the embodiments described herein provide systems and methods for measuring scattering patterns of defects and noise for wafer inspection.

The system includes a light source configured to generate light that is directed to the wafer. For example, in the embodiment of the system shown in FIG. 1, the system includes light source 100. In one embodiment, the light generated by the light source is incoherent light. Light source 100 may be an incoherent light source, which may include any such suitable light source known in the art. In one example, the light source may be a broadband plasma (BBP) light source that is configured to generate light at one or more wavelengths.

As shown in FIG. 1, the light from the light source may be directed to lens 102 that is configured to direct the light from the light source to one or more other elements of the system. Although lens 102 is shown in FIG. 1 as a single refractive optical element, lens 102 may, in practice, be one or more refractive optical elements and/or one or more reflective optical elements. The lens may include any suitable lens or lenses known in the art.

In one embodiment, the system includes an illumination aperture positioned in a path of the generated light that is directed to the wafer. For example, as shown in FIG. 1, the system may include illumination aperture 104, which may include a number of elements 106 that may be, for example, openings or light blocking elements. The illumination aperture may be positioned in illumination Fourier plane 108.

Methods and systems for optimizing an illumination aperture for broadband, incoherent light sources are described in U.S. Patent Application Publication No. 2014/0354983 to Kolchin et al. published on Dec. 4, 2014, which is incorporated by reference as if fully set forth herein. The embodiments described herein may be further configured as described in this publication. In this manner, the configuration of the illumination aperture used in the embodiments described herein may be determined as described in that publication. Although the above-referenced publication describes methods and systems for optimizing an illumination aperture, no systematic approach has been established for optimizing the aperture shape of the collection optical path. As such, the collection aperture optimization described further herein can be combined with the illumination aperture optimization methods described in that publication to form a rigorous method for optimizing simultaneously both collection and illumination apertures.

Light from the illumination aperture may be directed to a wafer by one or more additional optical elements of the system. For example, as shown in FIG. 1, the system may include beam splitter 108 that is configured to direct light from illumination aperture 104 to objective 110. Beam splitter 108 may include any suitable beam splitter known in the art such as a 50/50 beam splitter. Objective 110 may include any suitable refractive and/or reflective optical elements known in the art. Objective 110 may be configured to direct light to wafer 112 at any suitable angle(s) of incidence, which may be determined by the illumination aperture and one or more parameters of the objective. In some instances, the illumination aperture and objective may be configured for directional flood illumination of the wafer in which a relatively large area of the wafer is illuminated from a particular direction. Objective 110 may also be configured to collect light scattered and/or reflected from the wafer and to direct the collected light back through beam splitter 108. In this manner, the objective may be configured as a common mode objective.

In another embodiment, the light generated by the light source is coherent light, such as from a laser. In such an embodiment, lens 102 may include an optical element that directs collimated laser light to certain positions on pupil plane 108 or directly to wafer from a certain direction. Such embodiments may not therefore include an illumination aperture described herein.

The system may also include stage 114 on which wafer 112 is disposed during inspection. The stage may be coupled to a mechanical and/or robotic assembly (not shown) that is configured to move the stage (and therefore the wafer) such that light can be scanned over the wafer as the light from the wafer is collected and detected as described further herein.

The system also includes an optical element positioned in a collection pupil plane. For example, as shown in FIG. 1, the system may include optical element 116 positioned in collection pupil plane 118 such that light collected by objective 110 and transmitted by beam splitter 108 is directed to optical element 116. The optical element includes a set of collection apertures. For example, the optical element may include apertures 120 that may be configured as described further herein.

A number of different optical element configurations are described herein and even more optical element configurations are possible for use in wafer inspection systems. However, regardless of the particular optical element configuration, what each of the embodiments of the optical element have in common is that they are flexible in the scattering directions of the light that are allowed to pass through the optical element to the detector. As will be described further herein, some optical element embodiments may be flexible in that different components of the optical elements may be moved into or out of the collection pupil plane and therefore out of the path of the light from the wafer that is detected by the detector. However, the optical elements described herein may also or alternatively be flexible by allowing for a size, orientation, etc. of an opening or a light blocking element to be changed or such that different components of the optical element can be switched into and out of the collection pupil plane. The system may be configured to change the optical element configuration in any such manner using any suitable elements (not shown) such as one or more mechanical and/or robotic assemblies.

Although the optical element is described herein as using only mechanical means (e.g., openings or light blocking elements) to transmit light scattered at only selected scattering angles to a detector, the optical element may be configured in any other suitable manner to selectively transmit light at different positions within the collection pupil plane. For example, the optical element may be configured to selectively transmit light by refraction, absorption, diffraction, reflection, etc. In addition, although relatively simple, mechanical optical elements are described herein, the optical element may include other optical elements, which are not necessarily only mechanically based, such as electro-optic modulators, liquid crystal displays, micro-mirror arrays, etc. that can be used to transmit light in only certain portions of a collection pupil plane.

In one embodiment, the collection apertures include three or more slots. Each of the three or more slots extends across an entirety of the collection pupil plane in a first dimension, and the set of collection apertures extends across an entirety of the collection pupil plane in a second dimension perpendicular to the first dimension. One such embodiment of an optical element is shown in FIG. 2. As shown in this figure, optical element 200 includes 5 slots 1, 2, 3, 4, and 5. Although the optical element is shown in this figure as including 5 slots, the optical element may also include any other suitable number of slots. Each of the slots extends across an entirety of collection pupil plane 202 in dimension 204. In other words, each of the slots may have a length that covers an entirety of the collection pupil plane. In addition, as shown in this figure, the combination of the 5 slots extends across an entirety of dimension 206 of the collection pupil plane, and dimensions 204 and 206 are perpendicular to each other. In this manner, the combined width of each of the slots may cover an entirety of the collection pupil plane in one dimension.

In another embodiment, the collection apertures include two or more sets of slots. The slots in each of the two or more sets extend across only a portion of the collection pupil plane in a first dimension, and each of the two or more sets of slots extends across an entirety of the collection pupil plane in a second dimension perpendicular to the first dimension. One such embodiment of an optical element with two sets of slots is shown in FIG. 3. As shown in this figure, optical element 300 includes 10 slots, 1, 2, 3, 4, 5, 6, 7, 8, 9, and 10. Slots 1-5 are in one set of the slots, and slots 6-10 are in another set of the slots. The slots in both of the sets extend across only a portion of collection pupil plane 302 in first dimension 304. For example, as shown in FIG. 3, each of the sets of slots extends only halfway across the collection pupil plane in dimension 304, and the combination of the sets of slots extends across an entirety of the collection pupil plane in dimension 304. In addition, although each of the sets of slots is shown in FIG. 3 as extending across half of the collection pupil plane in dimension 304, the sets of slots may extend across any other portion of the collection pupil plane in this dimension. As further shown in FIG. 3, each of the sets of slots extends across an entirety of the collection pupil plane in second dimension 306 that is perpendicular to dimension 304. In this manner, the combined width of each of the slots in a set may cover an entirety of the collection pupil plane in the second dimension. Although each of the sets of slots are shown in FIG. 3 as including 5 slots, each of the sets of slots may include any other suitable number of slots. In addition, although the sets of slots are shown in FIG. 3 to include the same number of slots, different sets of slots may include different numbers of slots. Furthermore, although the slots in both of the sets are shown in FIG. 3 to have their lengths and widths oriented in the same directions, the slots in different sets may have their lengths and widths oriented in different directions (e.g., perpendicular directions).

In one embodiment, the collection apertures are openings that can be created in the optical element by moving one or more portions of the optical element out of the collection pupil plane. For example, in some embodiments described herein, the collection apertures may be openings that are created by moving one or more slots out of the collection pupil plane. In an additional embodiment, the collection apertures are light blocking regions that can be created in the optical element by moving one or more portions of the optical element into the collection pupil plane. For example, in some embodiments described herein, the collection apertures may be light blocking regions that are created by moving one or more slots into the collection pupil plane. The one or more portions of the optical elements may be moved into and out of the collection pupil plane in any suitable manner by the system or an element (not shown) of the system.

In some embodiments, the set of collection apertures includes a regular array of the collection apertures. The regular array of collection apertures may be a one-dimensional (1D) array as shown in FIG. 2 or a two-dimensional (2D) array as shown in FIG. 3. In this manner, the collection apertures may be oriented in a grid-like manner within the collection pupil plane. Such a configuration of the collection apertures may be advantageous for systematically imaging and analyzing the light that is scattered into different discrete scattering directions within the entire scattering hemisphere of the system, which may be performed as described further herein.

The system further includes a detector configured to detect light from the wafer that passes through the optical element when the optical element has different configurations thereby generating different images for the different configurations. For example, as shown in FIG. 1, the system may include lens 122 that is configured to image light from optical element 116 to detector 124. Although lens 122 is shown in FIG. 1 as a single refractive optical element, it may be configured as one or more refractive optical elements and/or one or more reflective optical elements. Detector 124 may include any suitable imaging detector such as a charge coupled device (CCD) or a time delay integration (TDI) camera. Preferably, the different images and any other experimental data are collected with the wafer stage position fixed and camera image vibration relatively small so that image misalignment between different apertures is negligible.

At least one of the different configurations of the optical element for which different images are generated includes only a single collection aperture in the set, and at least another of the different configurations includes two of the collection apertures in the set. For example, as described in further detail herein, the embodiments described herein are configured for determining the most suitable configuration for an optical element positioned in a collection pupil plane of a wafer inspection system and in order to experimentally gather sufficient data to make such a determination, in addition to images generated with a single opening or light blocking element in the collection pupil plane, images generated with more than one opening or light blocking element in the collection pupil plane are collected experimentally in order to accurately measure the phase relation between light scattered at different scattering angles.

In one embodiment, the different configurations include all possible combinations or pairs of the collection apertures in the set. For example, the set of images that are generated as described herein may contain phase relations for all possible pairs of scattering directions. All possible pairs of collection apertures for various optical element configurations described herein and images generated for such collection apertures are described further herein.

The system further includes a computer subsystem. For example, as shown in FIG. 1, the system includes computer subsystem 126. Computer subsystem 126 is configured to acquire the different images generated by the detector of the system. For example, different images generated by the detector for different configurations may be provided to computer subsystem 126. In particular, the computer subsystem may be coupled to the detector (e.g., by one or more transmission media shown by the dashed line in FIG. 1, which may include any suitable transmission media known in the art) such that the computer subsystem may receive the different images generated by the detector. The computer subsystem may be coupled to the detector in any other suitable manner. The computer subsystem may be further configured as described herein (e.g., as a processor included in a computer subsystem or system).

The computer subsystem is configured for constructing one or more additional images from two or more of the different images. The two or more different images used to generate any one of the one or more additional images do not include only the different images generated for single collection apertures in the set. For example, the set of images generated as described herein, which may contain phase relations for all possible pairs of scattering directions, may then be used to reconstruct the missing images for all other possible multi-hole (or multi-block) collection aperture combinations. In this manner, the embodiments described herein may be used to reconstruct images for a collection aperture of interest based on experimental data.

For wafer inspection, it is critical to separate DOIs from wafer noise. For dark field (DF) modes, where specular reflection is blocked, a critical factor is the difference in scattering directions, or profiles, of defects and noise. There are several approaches to measuring scattering patterns of defects and wafer noise. One way is to directly measure scattering intensity by imaging the collection pupil of an imaging system. The obvious advantage is the fact that the measurement is instantaneous and results in relatively high resolution in the Fourier domain. Therefore, pupil imaging can be used to measure diffraction orders or pupil signatures of noise scattering from relatively large uniform structures. The disadvantage of this technique is relatively low resolution in the imaging plane, which limits it to measuring pattern and noise scattering. In addition, this technique is highly susceptible to system artifacts such as ghost and flare.

The light scattering from relatively small defects is a coherent process even when the illumination light source is incoherent. The coherent process of defect light scattering causes the principal distinction in the way the collection pupil space is mapped and the collection aperture shape is optimized as compared to that of the illumination optical path. In particular, for incoherent light sources, different illumination directions are phase independent. Therefore, the mapping of the illumination pupil space and the illumination aperture optimization can be performed with pupil scanning pinhole type apertures.

In one such example, a single scanning pinhole aperture may be sufficient to map illumination pupil space on inspection systems that use incoherent light sources. In other words, to determine an optimum illumination aperture, a pinhole may be scanned across the pupil and then a map of defect signal may be created by mapping the defect images as a function of pinhole location in the illumination pupil. For example, two different (mutually exclusive) illumination apertures positioned in a Fourier plane may be used to separately generate different images for defects on a wafer. The two different images may then be used to determine what an image for the defects would look like if both of the illumination apertures were used simultaneously for image generation. In particular, since the illumination is incoherent, experimentally generated images for different, mutually exclusive illumination apertures can be summed to determine what an image generated with both illumination apertures would look like. In other words, for illumination aperture, a, that is mutually exclusive of illumination aperture, b, the image intensity in an image generated using both illumination apertures, a and b, can be determined as:

$$I_{ab}(x,y) = I_a + I_b$$

where $I_{ab}$ is the intensity of the image generated using both illumination apertures, a and b, $I_a$ is the intensity of the image generated using only illumination aperture, a, and $I_b$ is the intensity of the image generated using only illumination aperture, b. The image intensities are expressed as a function of within-image positions x and y.

Experiments performed by the inventors have shown that the difference between an image experimentally generated for two different, mutually exclusive illumination apertures and an image constructed from two different images, one experimentally generated for each illumination aperture, shows only uniform noise. Therefore, an image for two different, mutually exclusive illumination apertures that is constructed from two different, experimentally generated images, one for each illumination aperture, provides a suitable approximation of what the corresponding experimentally generated image would look like.

For collection aperture optimization, due to relatively strong interference between the waves scattered by a defect in different directions, the mapping of the collection pupil space cannot be done with only single scanning pinhole type apertures. Therefore, more elaborate aperture configurations should be additionally used, for example, double hole or double block type apertures to properly account for and to extract the interference terms and phase relation between different scattering directions and to differentiate and map the optical defect response in the collection pupil space.

In one such example, FIG. 4 shows two different collection aperture configurations 400 and 402 for the optical element configuration shown in FIG. 2. In configuration 400, the optical element is configured such that light passes through only slot 4. In contrast, in configuration 402, the optical element is configured such that light passes through only slot 2. Therefore, it would be useful if the images experimentally generated with these two collection aperture configurations and incoherent light could be summed to determine what an image generated when the optical element is configured such that light passes through slots 2 and 4 would look like.

However, even though an illumination source might generate incoherent light, light scattering from a defect is a coherent process that preserves phase. Therefore, images generated experimentally with different, mutually exclusive collection aperture configurations cannot just be summed to determine an image that would be generated using both of the different collection aperture configurations. For example, as shown in FIG. 4, image 404 was experimentally generated for a defect using collection aperture configuration 400 and image 406 was generated for the same defect using collection aperture configuration 402. However, as shown by image 408 that was experimentally generated for the same defect using collection aperture configuration 410, in which the optical element is configured such that light passes through both slots 2 and 4, image 408 does not appear to be equal to the sum of images 404 and 406.

Figure 5:
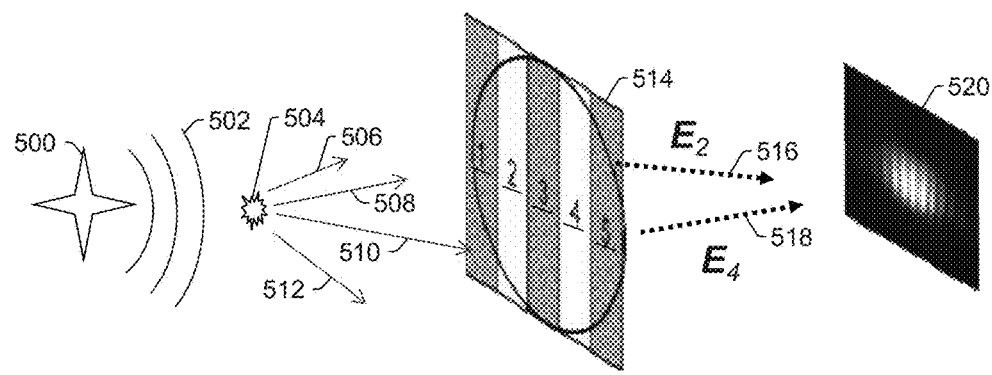
FIG. 5 is a schematic diagram illustrating a side view of one embodiment of the different configurations shown in FIG. 4 and how light passing through such an optical element configuration can cause interference at an image plane.

The reason why image 408 does not appear to be equal to the sum of images 404 and 406 is that even though the illumination source may generate incoherent light, light from a defect is a coherent process that preserves phase. This is shown schematically in FIG. 5. In particular, as shown in this figure, light source 500 may generate incoherent light 502 that can be directed to defect 504 on a wafer (not shown in FIG. 5). Light scattered from the defect at different scattering directions as shown by light 506, 508, 510, and 512 in FIG. 5 traveling along different propagation paths will have different electric field vectors or waves, E. There will, therefore, be relative phase, φ, between different electric field vectors or waves corresponding to different optical paths. As such, the electric field vector (or wave) and phase of the light scattered from the defect are not constant across the entirety of the collection pupil plane. Therefore, light that passes through different portions of an optical element positioned in the collection pupil plane may include light that is scattered by defects into different directions, which can have relatively strong phase relations. As a result, these waves can interfere with each other when combined on a detector's image plane thereby causing interference fringes in the images generated by the detector. In other words, the interference fringes in images may be the result of phase differences of waves exiting discrete sections of the optical element in the collection pupil plane. In the example shown in FIG. 5, optical element 514 positioned in a collection pupil plane (not shown in FIG. 5) may be configured such that light passes through slots 2 and 4 but not slots 1, 3, and 5. Therefore, light 516 exiting slot 2 may have electric field vector $E_2$, and light 518 exiting slot 4 may have electric field vector $E_4$. The phase relation between these two electric field vectors, phase$_{4,2}$, may then cause interference fringes in image 520 generated using such a collection pupil configuration. Therefore, the image intensity of image 520 may be expressed as $I_{24}(x,y)$ where $$I_{24}(x, y) = |E_4 + E_2|^2$$
$$= |E_4|^2 + |E_2|^2 + 2\mathrm{Re}\{E_4 E_2^*\}$$

where $2\mathrm{Re}\{E_4 E^*_2\}$ is the interference term $2|E_4 E_2|\cos(\mathrm{phase}_{4,2})$
where the amplitude of $E_4$ can be determined experimentally from an image generated using an aperture in which only light passing through slit 4 is detected, the amplitude of $E_2$ can be determined experimentally from an image generated using an aperture in which only light passing through slit 2 is detected, and Re is the real part of the complex number. As such, measurements using pairs of discrete openings or light blocking elements can be performed to reveal phase relation between light scattered into different parts of the collection pupil. That phase information can then be used to predict the best collection aperture(s) and their corresponding defect images.

Such image construction is not just limited to dark field (DF) images generated from scattered light. For example, such image construction may also be performed for bright field (BF) images that are generated from reflected light. In particular, the image intensity as a function of x,y position within the image can be determined for a BF image generated using the optical element configuration shown in FIG. 2 in which all of the slits are open using the following function:

$$I(x, y) = |E_5 + E_4 + E_3 + E_2 + E_1|^2$$

$$= \text{neglect } DF \text{ terms} =$$

$$= I_{12} + I_{13} + I_{14} + I_{15} - 3^*I_1$$

or generally $$I_{12345} = \Sigma_{k=1 \ldots 5} I_k + \Sigma_{k,s>k} \{I_{ks} - I_k - I_s\}.$$

Experiments performed by the inventors have shown that reconstructed BF images match substantially well with BF images acquired experimentally.

Therefore, an image that resembles an experimentally generated image for a collection aperture configuration that includes two or more openings through which light passes cannot be created from only images experimentally generated for only one of the openings. As such, in order to map light from wafers in collection pupil space, it is not sufficient to use only images generated using single collection aperture openings when combinations of openings are to be evaluated. In this manner, in order to relatively accurately map the collection pupil space, images for at least some double opening (e.g., slit) or light blocking element apertures should be generated experimentally so that reconstructed images can be generated relatively accurately. Different pairs of aperture measurements can then reveal the phase relation between different parts of the collection pupil.

Figure 6:
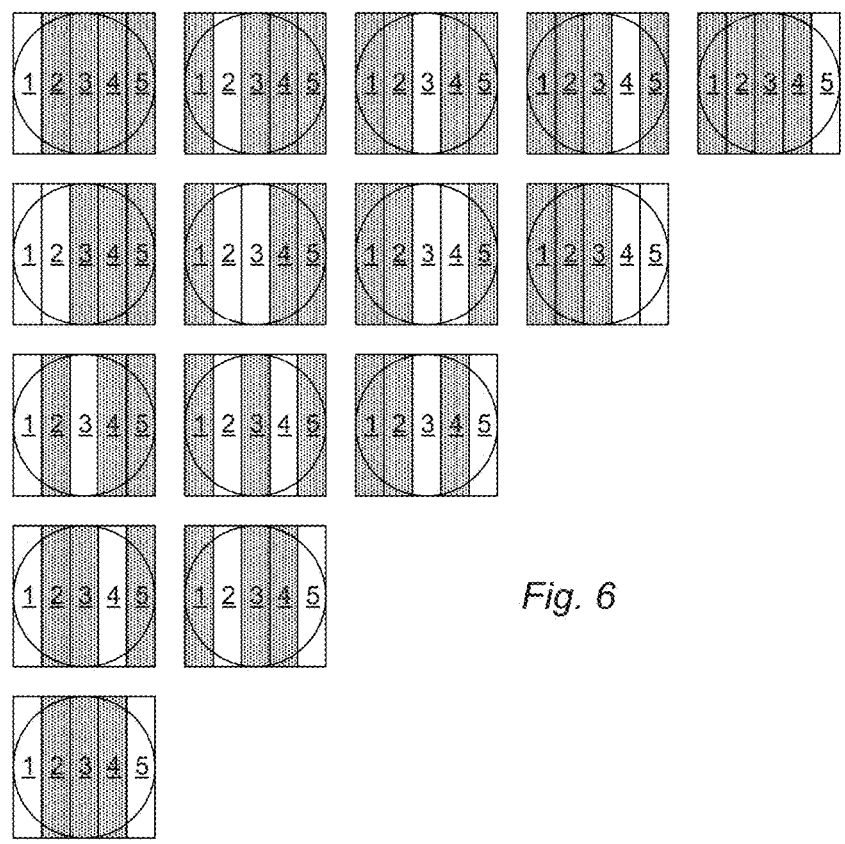
FIGS. 6-7 are schematic diagrams illustrating plan views of embodiments of different configurations of the optical element shown in FIG. 2.

With intensity and interference terms measured for all opening pairs, DOI images can be reconstructed for all possible aperture combinations. FIG. 6 shows all of the configurations of the optical element shown in FIG. 2 for which images can be generated experimentally such that all images that could possibly be needed for image reconstruction would be available. The slit combinations shown in FIG. 6 include all single and double slit apertures that may be used to acquire defect images. In particular, as shown in first row of configurations shown in FIG. 6, the configurations may include one each for each single slit aperture (in which light that passes through only a single slit is detected). As shown in the second row of this figure, the configurations used to experimentally generate images may include different pairs of slits, where the slits in any one pair are adjacent to each other in the optical element. In addition, as shown in the third row of this figure, the configurations used to experimentally generate images may also include additional pairs of slits in which the slits in any one pair are spaced from each other by another slit. Furthermore, as shown in the fourth row of this figure, the configurations used to experimentally generate images may include pairs of slits in which the slits in any one pair are spaced from each other by two slits. As further shown in the bottom row of this figure, the configurations used to experimentally generate images may also include a pair of slits in which the slits are spaced from each other by three slits.

The single slit and double slit combinations shown in FIG. 6, therefore, include all possible pairs of slits and therefore include all possible slit combinations that would be needed to reconstruct any images that could be generated by such an optical element. In this manner, images generated experimentally using only 15 different optical element configurations (i.e., for N=5 slits, the total number of single slits and slit pairs would be N(N+1)/2=15, whereas the total number of aperture configurations for this optical element would be 2^N-1=31) can be used to reconstruct any other images that might be considered. In this manner, for any one optical element configuration, an image that is either experimentally generated or reconstructed electronically would be available for use by the embodiments described herein.

In addition, as described further herein, different illumination aperture configurations can be considered with the different collection pupil plane configurations to thereby determine the best illumination and collection aperture configurations. If that is the case, then even if a significant number of illumination aperture configurations are to be considered (e.g., 20), the total number of physical aperture combinations may be relatively large (e.g., 15 collection apertures*20 illumination apertures=300 illumination/collection aperture combinations). However, since images can be generated for each combination relatively quickly (e.g., less than 1 second per image), experimentally generating images for all combinations may take less than 5 minutes. In addition, images may be generated experimentally or reconstructed for many but not all of the illumination apertures. Furthermore, for each illumination aperture configuration, images can be generated experimentally for each collection aperture configuration. However, unlike the collection aperture, different combinations of illumination apertures do not need to be used to experimentally generate images during data collection. Instead, during post-processing, the images can be combined (summed up) for the relevant combinations of illumination apertures as described further herein.

Even if the optical element configuration shown in FIG. 3 is used instead of that shown in FIG. 2 thereby doubling the sampling points in the collection pupil, the experimental data needed to reconstruct images for every possible combination of the same number of illumination apertures described above and every possible optical element configuration can be acquired relatively quickly and easily. For example, the optical element configuration shown in FIG. 3 has 55 double and single slit aperture combinations. Therefore, for 20 illumination apertures, the total number of physical aperture combinations for which images may be generated experimentally in order to be able to reconstruct any other image may be 20×55 or 1100 illumination aperture/collection aperture configurations. Since images can be generated for such a substantial number of configurations relatively quickly, the embodiments described herein can enable evaluation of every possible illumination aperture/collection aperture combination in a reasonable amount of time.

Figure 7:
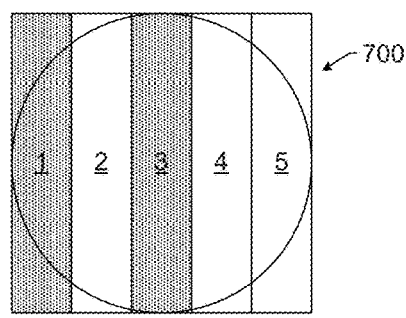

As described above, therefore, image reconstruction can be performed by constructing images for multi-slit apertures from single and double slit aperture images. One embodiment of a multi-slit aperture for which such an image can be reconstructed is shown in FIG. 7. In particular, in multi-slit aperture 700, the aperture is configured such that light passes through slits 2, 4, and 5 but is blocked by slits 1 and 3. The intensity of such an image can be expressed mathematically as a function of x,y positions within the image as follows:

$$I_{245}(x, y) = |E_5 + E_4 + E_2|^2$$

$$= |E_5|^2 + |E_4|^2 + |E_2|^2 +$$

$$2\text{Re}\{E_5 E_4^*\} + 2\text{Re}\{E_5 E_2^*\} + 2\text{Re}\{E_4 E_2^*\}$$

where $|E_5|^2$ can be determined experimentally as an image generated using an aperture in which only light passing through slit 5 is detected, $|E_4|^2$ can be determined experimentally as an image generated using an aperture in which only light passing through slit 4 is detected, and $|E_2|^2$ can be determined experimentally as an image generated using an aperture in which only light passing through slit 2 is detected. $\text{Re}\{E_5 E^*_4\}$ can be determined from an image generated using an aperture in which light passing through both slits 4 and 5 is detected, an image generated using an aperture in which light passing through only slit 5 is detected, and an image generated using an aperture in which light passing through only slit 4 is detected. $\text{Re}\{E_5 E^*_2\}$ can be determined from an image generated using an aperture in which light passing through both slits 2 and 5 is detected, an image generated using an aperture in which light passing through only slit 2 is detected, and an image generated using an aperture in which light passing through slit 5 is detected. $\text{Re}\{E_4 E^*_2\}$ can be determined from an image generated using an aperture in which light passing through both slits 4 and 2 is detected, an image generated using an aperture in which light passing through only slit 4 is detected, and an image generated using an aperture in which light passing through slit 2 is detected.

The computer subsystem is also configured for determining one or more characteristics of the different images and the one or more additional images and comparing the one or more characteristics of the different images and the one or more additional images. The one or more characteristics may include any suitable characteristics of the different and additional images and are preferably related to the defect detection that may be performed using the images. For example, the one or more characteristics may include signal, noise, signal-to-noise, signal minus noise, or some combination thereof. In this manner, the computer subsystem may be configured to analyze the optical response of the aperture based on the reconstructed image(s) as well as any experimentally generated images.

In some embodiments, the one or more characteristics of the different images and the additional image(s) may be determined by performing some defect detection method and/or algorithm on the images and then determining the characteristic(s) for any defects detected in the images. The computer subsystem may be configured to detect the defects in the images in any suitable manner using any suitable defect detection method(s) and/or algorithm(s). For example, the different images and the additional image(s) may be compared to a threshold and any of the portions of the images having a value above the threshold may be identified as a potential defect while the portions of the images that do not have a value above the threshold may not be identified as corresponding to potential defects. The value of the different images and the additional image(s) that is compared to the threshold may include, for example, intensity of pixels in the images. Appropriate values of the threshold may be determined in any suitable manner (e.g., as some multiple of the expected noise in the images). However, many other defect detection methods and/or algorithms are possible and the method and/or algorithm that is used with the images may be selected and/or determined based on the characteristics of the images possibly in combination with characteristics of the wafer and/or DOIs on the wafer. Once the defects have been detected in the images, the characteristic(s) of the images can be determined as described herein.

The computer subsystem is further configured for selecting one of the different or additional configurations for the optical element for inspection of the wafer based on results of the comparing. The different configurations may be the configurations for which images are generated experimentally, and the additional configurations may be configurations corresponding to the additional reconstructed images. In this manner, the system described herein for collection aperture and mode optimization, which may be called a "scatter and phase mapper," may include a set of special apertures installed in the collection path of the optical system, data acquisition components to support these apertures, and a computer subsystem for post-processing image reconstruction. The set of "scatter and phase mapper" apertures may include, but are not restricted to, all single hole and all double hole apertures. The holes may be defined on the grid in the collection pupil space.

In one embodiment, the selecting includes selecting the one of the different or additional configurations that produced the best values of the one or more characteristics for maximizing detection of DOIs on the wafer. For example, the one or more characteristics may be signal-to-noise ratio for one or more DOIs on the wafer. If there are multiple DOIs to be detected on the wafer, the one or more characteristics may be an average of the signal-to-noise ratios for the more than one DOI. Then, the aperture configuration corresponding to the highest signal-to-noise ratio for a DOI or the highest average signal-to-noise ratio for multiple DOIs may be selected. Other characteristics described herein may be used in a similar manner. As such, the images having the characteristics that will enable the best (maximum) DOI detection may be easily identified by the embodiments described herein. The aperture configurations corresponding to those images can then be selected for use in a wafer inspection recipe.

In another embodiment, the selecting includes selecting the one of the different or additional configurations that produced the best values of the one or more characteristics for minimizing detection of nuisance defects on the wafer. "Nuisance defects" as that term is used herein generally refers to events that are detected on a wafer that are not actually defects (e.g., but are just noise) or are defects that a user does not care about (e.g., non-DOI that do not affect yield of semiconductor manufacturing). In one example, the one or more characteristics may be a noise or average noise level in the images and then the configuration that produced the lowest noise or average noise level in the images may be selected. In another example, defect detection may be performed as described above using the images and then the configuration corresponding to the lowest nuisance capture rate may be selected for use in the wafer inspection. Furthermore, selecting the configuration for use in the wafer inspection system may be performed based on which configuration(s) provide the best DOI capture as well as the best nuisance suppression.

In one embodiment, the different images are generated for predetermined locations of defects on the wafer. For example, collection aperture optimization may include data collection for preselected defect locations on the wafer. The defect locations may be preselected in any suitable manner. In some instances, the image generation described herein may be performed for a wafer with one or more known defects located thereon so that the optical element configurations can be evaluated with respect to specific defects.

In another embodiment, the different images are generated with predetermined parameters for the light source, the detector, and any other optical elements of the system. In an additional embodiment, the different images are generated with different parameters for at least one of the light source, the detector, and any other optical elements of the system thereby generating different images for the different configurations and the different parameters, and the selecting includes selecting one combination of the one of the different or additional configurations for the optical element and one or more of the different parameters for the inspection of the wafer based on the results of the comparing. For example, collection aperture optimization may include data collection for preselected illumination aperture(s), spectral band(s), polarization state(s), and focus offset(s) for which the set of images with the "scatter and phase mapper" aperture set are collected. Then, for each reconstructed image and each preselected illumination aperture, spectrum, input and output polarization states, and focus offset, one or more characteristics such as those described herein may be calculated. A mode (defined by one set of values for the parameters) may then be selected such as the mode that gives the highest signal-to-noise ratio or signal-minus-noise for an individual defect or a group of defects (for example, DOIs) or the mode that gives the largest signal-to-noise ratio separation between a group of DOIs and nuisance defects. In this manner, the embodiments described herein may be used to find a best mode for wafer inspection, which may include a combination of spectral band, focus offset, and input and output polarizations in addition to the aperture shape to maximize the defect signal or signal-to-noise ratio. As such, mode selection (aperture, spectral band, focus offset, input and output polarization, etc.) may be performed based on the characteristics computed from reconstructed image(s) as well as other experimentally generated images described herein. In addition, mode selection described herein may be performed to simultaneously increase the capture rate of DOIs and suppress the capture rate of nuisances based on signal-to-noise values computed from reconstructed image(s) as well as other experimentally generated images described herein.

One advantage of selecting a mode in this manner is the implementation simplicity and fast computational speed. Another advantage of the embodiments described herein is that they can be used to improve sensitivity of wafer inspection tools including BF and/or DF tools. The embodiments can also be used to significantly simplify and reduce the time spent creating wafer inspection recipes for particular DOIs.

In some embodiments, the computer subsystem is configured for determining phase shift between the light scattered at different directions from the wafer based on the different images and determining one or more parameters of a phase contrast filter for use in the system during the inspection of the wafer based on the determined phase shift. For example, the embodiments described herein can be used to extract explicitly phase shift between different scattering directions (or phase relation of different scattering directions) based on experimental data. In particular, since interference fringes may be visible in the images experimentally generated and reconstructed by the embodiments described herein, the interference fringes can be used to determine information about the phase shift between the different scattering directions allowed to pass through the different optical element configurations corresponding to the images. This phase information can be then applied to design a phase contrast filter that maximizes defect signal. Such a phase contrast filter may then be positioned in the pupil plane of the collection optical path and can be used as a replacement of the collection aperture or in combination with the collection aperture in the pupil plane. For example, optical element 116 shown in FIG. 1 may be configured as such a phase contrast filter. The embodiments described herein can, therefore, be used to determine both phase shift and aperture shapes.

The embodiments described above may be configured for additional embodiments of measuring scattering patterns of defects and wafer noise for pupil mapping. The essence of this technique is to take a series of image plane measurements while varying Fourier plane parameters. The collection Fourier plane may be the same as collection pupil plane 118 in the system embodiment shown in FIG. 1. In one embodiment, the system is configured to cause the optical element to have the different configurations by stepping a square aperture across the collection pupil plane. For example, a square aperture can be stepped across the collection Fourier plane while an imaging camera is used to record resulting images. Subsequently, the defect response in the measured images can be used to reconstruct the scattering pattern. The advantage of this technique is relatively high resolution in the image plane, which allows measuring optical response of individual defects or structures. In order to measure defect scattering, specular reflection would typically be blocked.

In some embodiments, the different images are generated with different parameters for the illumination aperture by stepping a square aperture opening across an illumination pupil plane. For example, the simplest approach is the illumination-driven pupil mapper, where one illumination direction is opened at a time and a block is used in the collection Fourier plane to reject only specular reflection. This embodiment has an advantage of relatively high NA imaging, and it can be used to determine a preference for illumination direction for defects and noise in simple or suppressed patterns.

Figure 8:
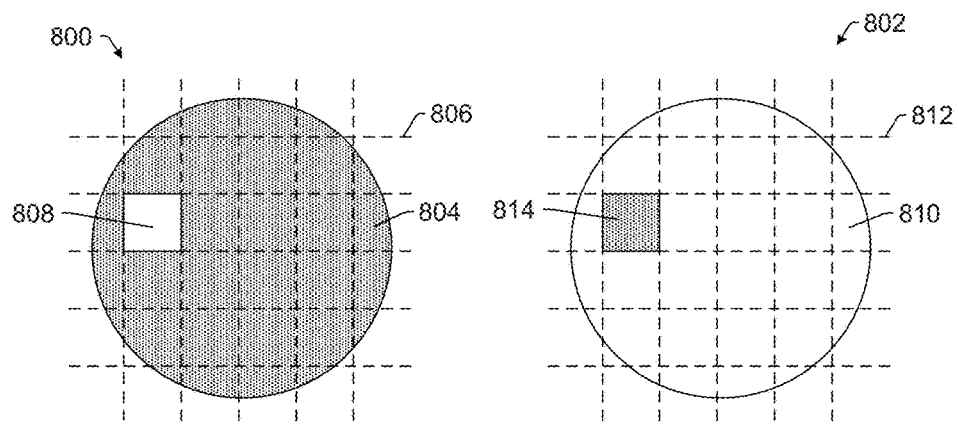
FIGS. 8-9 are schematic diagrams illustrating plan views of embodiments of an illumination aperture and an optical element that can be positioned in a collection pupil plane for the illumination aperture embodiments.

In one such example, FIG. 8 shows illumination aperture 800 and optical element 802 that may be positioned in the collection Fourier plane. In this manner, illumination aperture 800 may be used in place of illumination aperture 104 of the system shown in FIG. 1. In addition, the collection Fourier plane may be the same as the collection pupil plane. Therefore, optical element 802 may be positioned in plane 118 of the system shown in FIG. 1 thereby replacing optical element 116. As shown in FIG. 8, the illumination aperture may be configured to have a set of square apertures 804 defined by grid 806. The square apertures may be opened one at a time and images may be generated for each square aperture that is opened. In this manner, one NA area at a time within the objective may be used for illumination of the wafer. In addition, optical element 802 includes a set of square apertures 810 defined by grid 812. As shown in FIG. 8, the square apertures of the illumination aperture and the optical element have a 1:1 correspondence, meaning that their square apertures are defined on the same grid although there may be a difference in orientation, size, etc. between the two sets of square apertures due to the optical configuration of the system (e.g., rotation of the collection pupil plane relative to the illumination pupil plane, differences in magnification between collection and illumination, etc.). Nevertheless, as shown in FIG. 8, the square apertures cover an entirety of their respective illumination aperture and the optical element and can therefore be used to map the defect and wafer response to different illumination and scattering directions.

In one such embodiment, the different configurations for the optical element are created by stepping a single light blocking element across the collection pupil plane based on the stepping of the square aperture opening across the illumination pupil plane to thereby block specularly reflected light from the wafer due to illumination of the wafer with the different parameters for the illumination aperture. In the example shown in FIG. 8, square aperture 808 in the illumination aperture is opened thereby allowing light from a light source to illuminate a wafer (not shown in FIG. 8) while the remaining square apertures are closed. Therefore, in order to block the specular reflection from the wafer due to illumination through only square aperture 808, square aperture 814 of the optical element in the collection pupil plane may be closed while all other apertures of the optical element remain open. When the illumination aperture is changed so that illumination is directed through a different square aperture, the square aperture that is closed in the optical element may be changed accordingly so that the specular reflection due to the different illumination angle may be blocked. In this manner, the square apertures of the illumination aperture and the optical element can both be stepped across their corresponding pupil planes so that all of the scattered light from each possible illumination direction can be independently measured. Therefore, the embodiment shown in FIG. 8 may be used for an illumination-only scatter mapper in that light scattered in all scattering directions is collected and detected for each different illumination direction.

In one such embodiment, the different configurations for the optical element are created by placing one or more additional light blocking elements in the collection pupil plane based on the stepping of the square aperture opening across the illumination pupil plane to thereby block diffraction orders of the light from the wafer due to illumination of the wafer with the different parameters for the illumination aperture. In this embodiment of a pupil mapper, an additional Fourier filter may be used to suppress diffraction orders in the collection pupil. For example, in the embodiment shown in FIG. 9, when square aperture 808 is being used for illumination, square aperture 814 may be positioned in the collection pupil plane to block specular reflection and additional square aperture 900 may be positioned in the collection pupil plane to block a diffraction order of light from the wafer due to illumination with square aperture 808.

Depending on the structures formed on the wafer, one or more of the square apertures 810 of optical element 802 may be used to block diffraction orders of the light. For array structures with only one or two Fourier orders, a block or a plurality of blocks can be moved across the collection pupil to suppress diffraction orders. For more complex structures such as page breaks or gridded logic, a Manhattan blocker (e.g., a set of regularly spaced rods arranged in an orthogonal grid that can be used for suppression of 2D patterns or a cross centered on the $0^{th}$ order (specular) to block the primary diffraction orders from rectilinear patterns that appear similar to the gridded street and block pattern of Manhattan) can be used to suppress multiple diffraction orders in the x or y direction. In this manner, as the square aperture that is used for illumination is changed, the square apertures used in the collection pupil plane for blocking specular reflection and diffraction orders of light may be changed. Therefore, this configuration can be used to measure only scattered light due to illumination from discrete illumination angles that is sequentially directed to the wafer. Pupil imaging described previously can be used with this technique to aid diffraction order blocking.

In another such embodiment, while the illumination aperture has one set of the different parameters for the illumination aperture, the different images are generated with the different configurations for the optical element by stepping one or more additional light blocking elements across the collection pupil plane. For example, in another embodiment of the pupil mapper, the illumination and collection can be measured independently. In particular, illumination and collection Fourier plane signatures can be independent of each other. In order to measure such signatures, a block additional to the specular blocker may be stepped across the collection pupil, while an imaging camera is used to record the resulting images. This process may then be repeated for each illumination direction, and the measured images can be used to reconstruct the defect scattering pattern.

Figure 9:
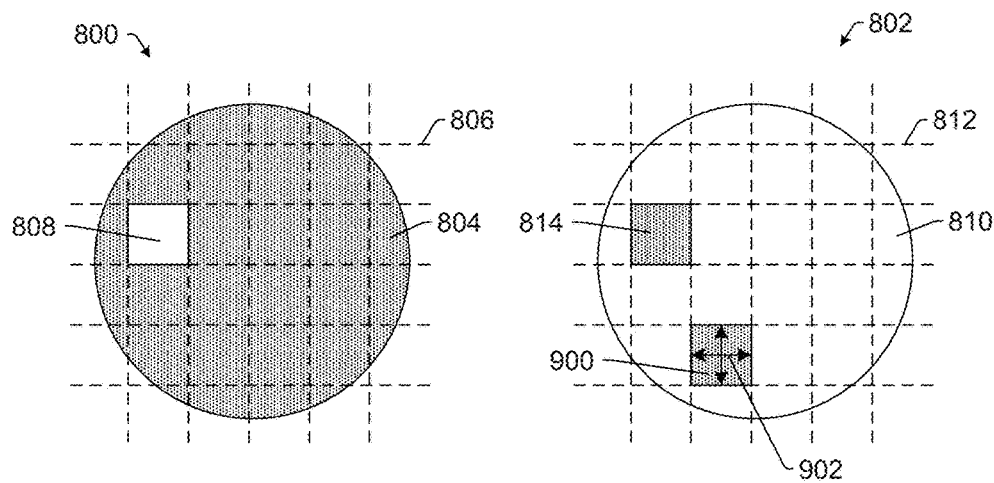

For example, in the embodiment shown in FIG. 9, when square aperture 808 is being used for illumination, square aperture 814 may be positioned in the collection pupil plane to block specular reflection and additional square aperture 900 may be moved around the collection pupil plane while square aperture 808 continues to be used for illumination. In other words, the position of the square aperture that is opened for illumination may be held constant while an additional collection block is stepped across the collection pupil as shown by arrows 902. In this manner, the additional block may be moved around the collection while the subset of illumination angles used for illumination is held constant. As such, the embodiments described herein provide a pupil mapper that can be used to measure illumination and collection independently.

Such embodiments can be particularly useful since illumination and collection Fourier plane signatures can be independent of each other. For example, one of the challenges of wafer inspection is separation of defects from the overwhelming surrounding noise. Simulations show that one of the properties that can be used for this separation is scattering profiles that are different for various defect or noise types. For example, surface roughness noise might preferentially exhibit forward scattering, while protrusion type defects may preferentially exhibit backward scattering. This difference may be exploited by a collection aperture that blocks forward scattering thereby reducing noise contributions.

In another example, different types of roughness can exhibit different types of scattering. For example, three types of roughness, line edge roughness (LER), line width roughness (LWR), and surface roughness (SUR) were simulated with different statistical parameters on 20 nm design rule line space arrays of two different materials, silicon and silicon dioxide, on a silicon substrate. The light distribution on the collection pupil plane was then calculated for different coherent illumination directions. These simulations and calculations showed that roughness induced scattering is strongly direction dependent. For example, LWR scattering is much weaker for illumination with polarization along the lines for silicon line space arrays. In contrast, surface roughness scattering behaves differently. For silicon dioxide line space arrays, it is difficult to tell any polarization preference for any types of roughness. In the statistical parameter range of interest, LER root-mean-square (RMS) changes only the scattering intensity but not the scattering distribution pattern while LER correlation length affects both the scattering intensity and the scattering pattern. Therefore, information about such scattering intensity and patterns can be measured as described herein to thereby determine a collection pupil plane configuration that will suppress as much roughness related noise in the images as possible. Suppressing this and other sources of noise will enable better detection of DOIs through enhanced defect signals (or signal-to-noise).

Although some of the embodiments are described above with respect to square apertures, the embodiments described above may also be implemented with any of the other illumination aperture and optical element configurations described herein. For example, in some embodiments, the different images are generated with different parameters for the illumination aperture, which may be varied as described further herein.

In one such embodiment, the different configurations for the optical element are determined based on the different parameters for the illumination aperture to thereby block specularly reflected light from the wafer due to illumination of the wafer with the different parameters for the illumination aperture. Any of the optical element configurations described herein may be determined and varied to block specularly reflected light due to different illumination parameters. In some such embodiments, the different configurations for the optical element are determined based on the different parameters for the illumination aperture to thereby block diffraction orders of the light from the wafer due to illumination of the wafer with the different parameters for the illumination aperture. Any of the optical element configurations described herein may be determined and varied to block specularly diffracted light due to different illumination parameters.

In another such embodiment, while the illumination aperture has one set of the different parameters for the illumination aperture, the different images are generated with the different configurations for the optical element. For example, any of the optical element configurations described herein may be varied such that different images can be generated experimentally for different collection pupil plane configurations and the same illumination pupil plane configuration.

Because pupil mapper resolution in Fourier space is limited to the number of discrete steps or measurements across the pupil, the choice of coordinate system is of high importance. For example, in one embodiment, the different configurations of the optical element are determined in a Cartesian coordinate system when the optical element will be performing Fourier filtering during the inspection of the wafer. In particular, for Fourier filtering, a Cartesian coordinate system may be preferable. In an additional embodiment, the different configurations of the optical element are determined in a polar coordinate system when the computer subsystem is configured for mapping defect scattering in the different images. For example, for mapping defect scattering, polar coordinates may be more suitable.

In some embodiments, the different configurations of the optical element correspond to different positions and/or sizes of an opening or a light blocking element in the collection pupil plane. For example, variations to the previous embodiments are a slit or opening in a collection Fourier plane with variable position and size that can be used to measure illumination and collection independently. Instead of blocking certain scattering directions, it would open discrete parts of the collection Fourier space thereby allowing for measuring of scattering behavior.

A goal of measuring scattering patterns as described herein is often an aperture or set of apertures used to detect DOIs and suppress noise. Therefore, a flexible aperture mechanism may be desirable for timely implementation of recommended aperture sets. One embodiment of such a flexible mechanism is a set of wheels and sliders that can be moved in the x and/or y direction. By placing basic shapes on such sliders and combining them, desired apertures may be configured. In some embodiments, the set of collection apertures includes a canonical set of discrete apertures. For example, another embodiment of a flexible aperture mechanism is a canonical set of discrete apertures that can be used to collect basic types of scattering, for example, forward scattering or backward scattering.

Figure 10:
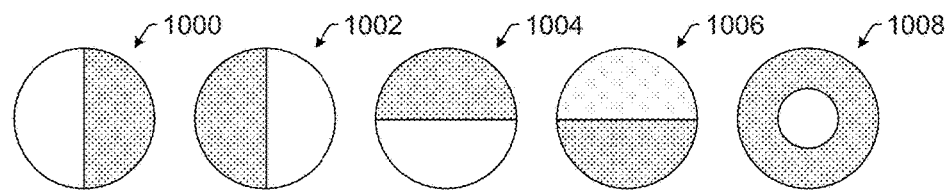
FIG. 10 is a schematic diagram illustrating plan views of an embodiment of a canonical set of discrete apertures that may be included in a set for the optical element.

FIG. 10 illustrates one embodiment of such apertures. For example, as shown in FIG. 10, a canonical set of apertures may include apertures 1000, 1002, 1004, 1006, and 1008. Depending on the direction of illumination, apertures 1000 and 1002 can be used to measure forward or backward scattering while apertures 1004 and 1006 may be used to measure side scattering on different sides of an illumination plane. In addition, a canonical set of apertures may include only one such aperture if the system also includes a mechanism such as that described further herein to alter a position of the aperture in the collection pupil plane. The canonical set of apertures may also include other aperture shapes such as circular aperture 1008 shown in FIG. 10. Again, if the circular aperture is flexible, then the system may alter the position and/or size of the circular aperture in the collection pupil plane such that scattering to different directions in the collection pupil plane can be measured.

Each of the system embodiments described herein may be further configured according to any other embodiment(s) described herein. In addition, each of the system embodiments described herein may be configured to perform one or more of the method embodiments described herein.

Figure 11:
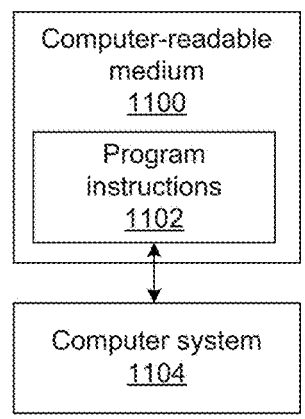
FIG. 11 is a block diagram illustrating one embodiment of a non-transitory computer-readable medium that includes program instructions executable on a computer system for performing one or more of the computer-implemented method embodiments described herein.

Another embodiment relates to a non-transitory computer-readable medium storing program instructions executable on a computer system for performing a computer-implemented method for determining a configuration for an optical element positioned in a collection aperture during wafer inspection. One such embodiment is shown in FIG. 11. For example, as shown in FIG. 11, computer-readable medium 1100 stores program instructions 1102 executable on computer system 1104 for performing the computer-implemented method that includes acquiring different images for a wafer.

In this manner, the embodiments described herein can be implemented in two different stages that can be performed by two different systems or methods. For example, one system or method may be configured to perform the data acquisition stage where the defect images are collected for the selected illumination apertures and the set of collection apertures used for experimental image generation. Another system or method may be configured to perform the data post-processing stage that can be implemented in the form of a software package that provides mode recommendations based on the input data.

The different images were generated by directing light generated by a light source to the wafer and detecting light from the wafer that passes through an optical element when the optical element has different configurations thereby generating the different images for the different configurations. The optical element and the different configurations may include any of those described herein. Directing the light and detecting the light may be further performed as described herein. The light source may include any light sources described herein. The computer-implemented method also includes constructing one or more additional images, determining one or more characteristics, comparing the one or more characteristics, and selecting one of the different or additional configurations, which may be performed as described further herein. The computer-implemented method may include any other step(s) of any other method(s) described herein.

Program instructions 1102 implementing methods such as those described herein may be stored on computer-readable medium 1100. The computer-readable medium may be a storage medium such as a magnetic or optical disk, or a magnetic tape or any other suitable non-transitory computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 1104 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

An additional embodiment relates to a method for determining a configuration for an optical element positioned in a collection aperture during wafer inspection. The method includes directing light generated by a light source to a wafer. The light source may be configured as described herein. The method also includes detecting light from the wafer that passes through an optical element when the optical element has different configurations thereby generating different images for the different configurations. The optical element may include any of the optical elements described herein. The different configurations may include any of those described herein.

The method also includes constructing one or more additional images from two or more of the different images. The two or more different images used to generate any one of the one or more additional images do not include only the different images generated for single collection apertures in the set. The method further includes determining one or more characteristics of the different images and the one or more additional images. In addition, the method includes comparing the one or more characteristics of the different images and the one or more additional images. The method also includes selecting one of the different or additional configurations for the optical element for inspection of the wafer based on results of the comparing step. The constructing, determining, comparing, and selecting steps are performed by a computer system, which may be configured as any of the computer subsystems or systems described herein.

Each of the steps of the method described above may be performed as described further herein. The method described above may include any other step(s) of any other method(s) described herein. The method described above may be performed using any of the systems described herein.

The methods described herein may also include storing results of any of the step(s) of any of the methods in a computer-readable storage medium. The results may include any of the results described herein and may be stored in any manner known in the art. The storage medium may include any suitable storage medium known in the art. After the results have been stored, the results can be accessed in the storage medium and used as described herein, formatted for display to a user, used by another software module, method, or system, etc.

Further modifications and alternative embodiments of various aspects of the invention will be apparent to those skilled in the art in view of this description. For example, methods and systems for determining a configuration for an optical element positioned in a collection aperture during wafer inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to determine a configuration for an optical element positioned in a collection aperture during wafer inspection, comprising:

a light source configured to generate light that is directed to the wafer;

an optical element positioned in a collection pupil plane, wherein the optical element comprises a set of collection apertures;

a detector configured to detect light from the wafer that passes through the optical element when the optical element has different configurations thereby generating different images for the different configurations, wherein at least one of the different configurations comprises only a single collection aperture in the set, and wherein at least another of the different configurations comprises two of the collection apertures in the set; and a computer subsystem configured for:

constructing one or more additional images from two or more of the different images, wherein the two or more different images used to generate any one of the one or more additional images do not comprise only the different images generated for single collection apertures in the set;

determining one or more characteristics of the different images and the one or more additional images;

comparing the one or more characteristics of the different images and the one or more additional images; and selecting one of the different or additional configurations for the optical element for inspection of the wafer based on results of said comparing.

2. The system of claim 1, wherein the collection apertures comprise three or more slots, wherein each of the three or more slots extends across an entirety of the collection pupil plane in a first dimension, and wherein the set of collection apertures extends across an entirety of the collection pupil plane in a second dimension perpendicular to the first dimension.

3. The system of claim 1, wherein the collection apertures comprise two or more sets of slots, wherein the slots in each of the two or more sets extends across only a portion of the collection pupil plane in a first dimension, and wherein each of the two or more sets of slots extends across an entirety of the collection pupil plane in a second dimension perpendicular to the first dimension.

4. The system of claim 1, wherein the light generated by the light source is incoherent light.

5. The system of claim 1, wherein the light generated by the light source is coherent light.

6. The system of claim 1, wherein said selecting comprises selecting the one of the different or additional configurations that produced the best values of the one or more characteristics for maximizing detection of defects of interest on the wafer.

7. The system of claim 1, wherein said selecting comprises selecting the one of the different or additional configurations that produced the best values of the one or more characteristics for minimizing detection of nuisance defects on the wafer.

8. The system of claim 1, wherein the collection apertures are openings that can be created in the optical element by moving one or more portions of the optical element out of the collection pupil plane.

9. The system of claim 1, wherein the collection apertures are light blocking regions that can be created in the optical element by moving one or more portions of the optical element into the collection pupil plane.

10. The system of claim 1, wherein the set of collection apertures comprises a regular array of the collection apertures.

11. The system of claim 1, wherein the different images are further generated for predetermined locations of defects on the wafer.

12. The system of claim 1, wherein the different images are further generated with predetermined parameters for the light source, the detector, and any other optical elements of the system.

13. The system of claim 1, wherein the different images are further generated with different parameters for at least one of the light source, the detector, and any other optical elements of the system thereby generating different images for the different configurations and the different parameters, and wherein said selecting comprises selecting one combination of the one of the different or additional configurations for the optical element and one or more of the different parameters for the inspection of the wafer based on the results of said comparing.

14. The system of claim 1, wherein the different configurations further comprise all possible combinations of the collection apertures in the set.

15. The system of claim 1, wherein the computer subsystem is further configured for determining phase shift between the light scattered at different directions from the wafer based on the different images and determining one or more parameters of a phase contrast filter for use in the system during the inspection of the wafer based on the determined phase shift.

16. The system of claim 1, wherein the system is further configured to cause the optical element to have the different configurations by stepping a square aperture across the collection pupil plane.

17. The system of claim 1, further comprising an illumination aperture positioned in a path of the generated light that is directed to the wafer, wherein the different images are further generated with different parameters for the illumination aperture.

18. The system of claim 17, wherein the different configurations for the optical element are determined based on the different parameters for the illumination aperture to thereby block specularly reflected light from the wafer due to illumination of the wafer with the different parameters for the illumination aperture.

19. The system of claim 18, wherein the different configurations for the optical element are determined based on the different parameters for the illumination aperture to thereby block diffraction orders of the light from the wafer due to illumination of the wafer with the different parameters for the illumination aperture.

20. The system of claim 18, wherein, while the illumination aperture has one set of the different parameters for the illumination aperture, the different images are further generated with the different configurations for the optical element.

21. The system of claim 1, further comprising an illumination aperture positioned in a path of the generated light that is directed to the wafer, wherein the different images are further generated with different parameters for the illumination aperture by stepping a square aperture opening across an illumination pupil plane.

22. The system of claim 21, wherein the different configurations for the optical element are created by stepping a single light blocking element across the collection pupil plane based on the stepping of the square aperture opening across the illumination pupil plane to thereby block specularly reflected light from the wafer due to illumination of the wafer with the different parameters for the illumination aperture.

23. The system of claim 22, wherein the different configurations for the optical element are created by placing one or more additional light blocking elements in the collection pupil plane based on the stepping of the square aperture opening across the illumination pupil plane to thereby block diffraction orders of the light from the wafer due to illumination of the wafer with the different parameters for the illumination aperture.

24. The system of claim 22, wherein, while the illumination aperture has one set of the different parameters for the illumination aperture, the different images are further generated with the different configurations for the optical element by stepping one or more additional light blocking elements across the collection pupil plane.

25. The system of claim 1, wherein the set of collection apertures comprises a canonical set of discrete apertures.

26. The system of claim 1, wherein the different configurations of the optical element are determined in a Cartesian coordinate system when the optical element will be performing Fourier filtering during the inspection of the wafer.

27. The system of claim 1, wherein the different configurations of the optical element are determined in a polar coordinate system when the computer subsystem is further configured for mapping defect scattering in the different images.

28. The system of claim 1, wherein the different configurations of the optical element correspond to different positions of an opening in the collection pupil plane.

29. The system of claim 1, wherein the different configurations of the optical element correspond to different sizes of an opening in the collection pupil plane.

30. The system of claim 1, wherein the different configurations of the optical element correspond to different positions of a light blocking element in the collection pupil plane.

31. The system of claim 1, wherein the different configurations of the optical element correspond to different sizes of a light blocking element in the collection pupil plane.

32. The sys of claim 1, wherein the light source comprises a broadband light source.

33. The system of claim 1, wherein the light source comprises a laser.

34. The system of claim 1, wherein the detected light comprises scattered light.

35. The system of claim 1, wherein the detected light comprises reflected light.

36. The system of claim 1, wherein the detector is further configured to detect the light in a dark field mode.

37. The system of claim 1, wherein the different images comprise dark field images.

38. The system of claim 1, wherein the different images comprise bright field images.

39. A non-transitory computer-readable medium, storing program instructions executable on a computer system for performing a computer-implemented method for determining a configuration for an optical element positioned in a collection aperture during wafer inspection, wherein the computer-implemented method comprises:

acquiring different images for a wafer, wherein the different images were generated by:
 directing light generated by a light source to the wafer; and
 detecting light from the wafer that passes through an optical element when the optical element has different configurations thereby generating the different images for the different configurations, wherein the optical element is positioned in a collection pupil plane, wherein the optical element comprises a set of collection apertures, wherein at least one of the different configurations comprises only a single collection aperture in the set, and wherein at least another of the different configurations comprises two of the collection apertures in the set;

constructing one or more additional images from two or more of the different images, wherein the two or more different images used to generate any one of the one or more additional images do not comprise only the different images generated for single collection apertures in the set;

determining one or more characteristics of the different images and the one or more additional images;

comparing the one or more characteristics of the different images and the one or more additional images; and selecting one of the different or additional configurations for the optical element for inspection of the wafer based on results of said comparing.

40. A method for determining a configuration for an optical element positioned in a collection aperture during wafer inspection, comprising:

directing light generated by a light source to a wafer;

detecting light from the wafer that passes through an optical element when the optical element has different configurations thereby generating different images for the different configurations, wherein the optical element is positioned in a collection pupil plane, wherein the optical element comprises a set of collection apertures, wherein at least one of the different configurations comprises only a single collection aperture in the set, and wherein at least another of the different configurations comprises two of the collection apertures in the set;

constructing one or more additional images from two or more of the different images, wherein the two or more different images used to generate any one of the one or more additional images do not comprise only the different images generated for single collection apertures in the set;

determining one or more characteristics of the different images and the one or more additional images;

comparing the one or more characteristics of the different images and the one or more additional images; and selecting one of the different or additional configurations for the optical element for inspection of the wafer based on results of said comparing, wherein said constructing, said determining, said comparing, and said selecting are performed by a computer system.

* * * * *